(12) United States Patent
Vishnupad et al.

(10) Patent No.: US 7,662,855 B2
(45) Date of Patent: Feb. 16, 2010

(54) RETINOID SOLUTIONS AND FORMULATIONS MADE THEREFROM

(75) Inventors: Mohan Vishnupad, Easton, CT (US); Naomi Vishnupad, Easton, CT (US)

(73) Assignee: Imaginative Research Associates, Inc., Woburn, MA (US)

( * ) Notice: Subject to any disclaimer, the term of this patent is extended or adjusted under 35 U.S.C. 154(b) by 0 days.

(21) Appl. No.: 10/984,630

(22) Filed: Nov. 9, 2004

(65) Prior Publication Data

US 2005/0255130 A1    Nov. 17, 2005

Related U.S. Application Data

(60) Provisional application No. 60/569,809, filed on May 11, 2004.

(51) Int. Cl.
    *A61K 31/20* (2006.01)
    *A01N 31/04* (2006.01)
    *A61K 31/74* (2006.01)

(52) U.S. Cl. .................. 514/559; 514/725; 514/859; 514/970; 514/912; 424/78.04

(58) Field of Classification Search ............... 514/559, 514/725, 859, 970, 912; 424/78.04
    See application file for complete search history.

(56) References Cited

U.S. PATENT DOCUMENTS

| | | | |
|---|---|---|---|
| 3,729,568 A | 4/1973 | Kligman | |
| 3,906,108 A | 9/1975 | Felty | |
| 4,247,547 A | 1/1981 | Marks | |
| 4,593,048 A * | 6/1986 | Sato et al. | 514/778 |
| 4,603,146 A | 7/1986 | Kligman | |
| 4,826,828 A | 5/1989 | Wilmott et al. | |
| 5,034,228 A | 7/1991 | Meybeck et al. | |
| 5,145,675 A * | 9/1992 | Won | 424/78.31 |
| 5,559,149 A | 9/1996 | Clum et al. | |
| 5,690,923 A | 11/1997 | DeVringer et al. | |
| 5,721,275 A | 2/1998 | Bazzano | |
| 6,136,332 A * | 10/2000 | Grollier et al. | 424/404 |
| 6,387,383 B1 * | 5/2002 | Dow et al. | 424/401 |
| 6,461,622 B2 * | 10/2002 | Liu et al. | 424/401 |
| 6,517,847 B2 * | 2/2003 | Dow et al. | 424/401 |
| 6,531,141 B1 | 3/2003 | Marvel | |
| 6,774,100 B2 * | 8/2004 | Vishnupad | 510/407 |
| 2002/0082745 A1 | 6/2002 | Wilmott et al. | |
| 2002/0110594 A1 | 8/2002 | Vishnupad | |
| 2002/0193321 A1 | 12/2002 | Vishnupad et al. | |
| 2003/0004118 A1 | 1/2003 | Vishnupad et al. | |
| 2003/0215493 A1 * | 11/2003 | Patel | 424/450 |

FOREIGN PATENT DOCUMENTS

| | | |
|---|---|---|
| EP | 0 566 405 A2 | 4/1993 |
| WO | WO 03/082703 A1 | 9/2003 |
| WO | WO 2004/054543 A1 | 7/2004 |

OTHER PUBLICATIONS

Ramchandi, M., et al. "Formulation of Topical Drug Delivery Systems." Transdermal and Topical Drug Delivery Systems. Eds. Tapash K Ghosh, William R. Pfister, and Su Il Yum. Boca Raton: Taylor & Francis Group, 1997. 539-578.*

Nairn, J. G. "Solutions, Emulsions, Suspensions and Extracts." Remington: The Science and Practice of Pharmacy. Ed. Alfonso R. Gennaro. Easton: Mack, 1995. 1509-1515.*

* cited by examiner

*Primary Examiner*—Sreeni Padmanabhan
*Assistant Examiner*—Umamaheswari Ramachandran
(74) *Attorney, Agent, or Firm*—Carter, DeLuca, Farrell & Schmidt, LLP

(57) ABSTRACT

Compositions for topical application for treating a skin disorder (e.g., acne) include a retinoid, which is solubilized completely in alcohol only with the aid of cosolvents such as esters (e.g., alkyl benzoate, isopropyl palmitate, isopropyl myristate, diisopropyl adipate and their derivatives). This completely solubilized retinoid can be used to formulate an emulsion system or liquid to powder suspension containing a second active, such as an antibiotic (e.g., clindamycin).

5 Claims, 3 Drawing Sheets

RETINOID SOLUTIONS AND FORMULATIONS MADE THEREFROM

RELATED APPLICATIONS

This application claims priority to U.S. Provisional application Ser. No. 60/569,809 filed May 11, 2004, the entire disclosure of which is incorporated herein by this reference.

BACKGROUND OF RELATED ART

The combination of retinoids and antibiotics is of great interest in dermatology, due to the established synergistic efficacy of the two actives in treating acne. Retinoids are powerful keratolytic agents and antibiotics provide anti-bacterial activity for treating acne. Antibiotics such as erythromycin and clindamycin are soluble in aqueous media. Retinoids are insoluble in water. When formulating combination actives for treating acne, it is important to keep the retinoids in complete solution as well as antibiotics in solution. For example, aqueous retinoid acid formulations containing no alcohol and no fats have not shown to be clinically efficacious because the active ingredients are not dissolved in solution, and therefore not available for effectively treating the skin. See, U.S. Pat. No. 5,690,923.

Unfortunately, retinoids alone in formulations have been known to be quite unstable. The stabilization of retinoids by dissolving in alcohols has been proposed. For example, U.S. Pat. No. 5,721,275 discloses a topical composition containing a retinoid as a single active ingredient wherein in large concentrations of alcohol are used to dissolve the retinoids in solution. However, the stability of the composition containing high levels of alcohol is limited and high levels of alcohol will irritate the skin. Retinoids have also been formulated in aqueous vehicles using surfactants. For example, U.S. Pat. No. 5,690,923 discloses the use of surfactants such as ethoxylated alcohol, ethers, and block polymers to solubilize retinoids in water without using any alcohol.

There exists room for improvement in the area of formulating, packaging, storing and dispensing compositions containing both retinoids and antibiotics to satisfactorily provide a full two year expiration date. Specifically, a need exists for a composition containing a retinoid and an antibiotic in complete solution, in which both active are chemically and physically stable.

SUMMARY

Solutions of retinoic acid, tretinoin and other retinoids that are not completely soluble in alcohol are provided. The solutions include anhydrous alcohol in an amount insufficient alone to solubilize the retinoid and an ester co-solvent. The solutions can be used alone or to formulate topical compositions, such as emulsions or suspensions. In particularly useful embodiments, the formulations contain a water-soluble active in an aqueous phase and the retinoid solution in a non-aqueous phase.

In some embodiments, the present retinoid solutions are dispersed via a chamber in chamber pump delivery system.

The present compositions do not use any surfactants or emulsifiers to solubilize retinoids. Rather, the present retinoid solutions employ cosolvents, (such as alkyl benzoate, isopropyl palmitate ("IPP"), isopropylmyristate ("IPM"), diisopropyl adipate, or their derivatives) in conjunction with a small amount of alcohol. A benefit of the present solutions is that the amount of alcohol employed in the emulsion or suspension is so insignificant that the alcohol induced skin irritation is eliminated.

DETAILED DESCRIPTION OF PREFERRED EMBODIMENTS

Figure 1:
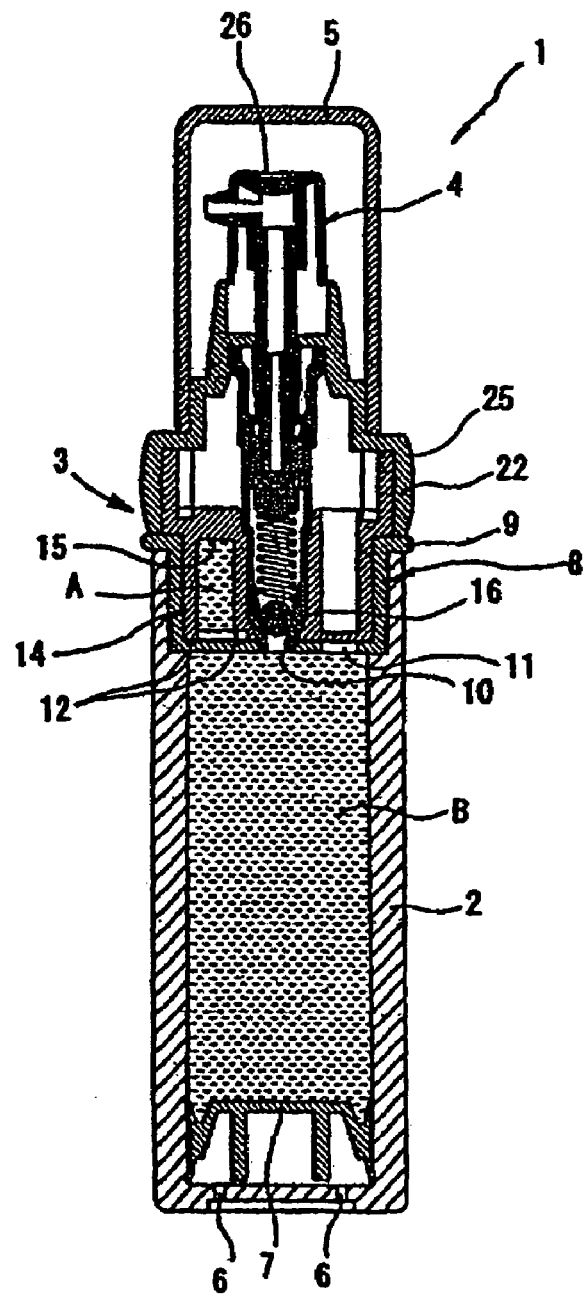
FIG. 1 shows one type of dispenser suitable for packaging and delivering formulations containing the present retinoid solutions.

Solutions of retinoids in accordance with this disclosure contain anhydrous alcohol in an amount insufficient alone to solubilize the retinoid, and an ester co-solvent.

The retinoid can be any retinoid that provides a benefit to a user upon topical application and is not completely soluble in alcohol. Suitable materials include, but are not limited to retinoic acid, retinyl palmitate, retinyl propionate, retinyl acetate, tretinoin, isotretinoin, motretinide, adapalene, tazarotene, azelaic acid as well as synthetic retinoid mimetics.

The anhydrous alcohol is present in an amount insufficient alone to solubilize the retinoid. At such low levels, the amount of alcohol present is less likely to be sufficient to irritate the skin of a user. Suitable anhydrous alcohols include anhydrous ethanol and anhydrous isopropanol.

The cosolvent can be any material which, when combined with the small amount of anhydrous alcohol, completely solubilizes the retinoid. Particularly useful cosolvents include esters, such as alkyl benzoates, isopropyl palmitate ("IPP"), isopropyl myristate ("IPM"), diisopropyl adipate and their derivatives. Long chain alkylbenzoates are one type of benzoic acid ester useful as a co-solvent in preparing the present retinoid solutions. The alkyl group of the alkyl benzoate preferably contains from 12 to 15 carbon atoms. Suitable alkyl benzoates are commercially available, for example, under the tradename FINSOLV (Finetex, Inc., Elmwood Park, N.J.) such as FINSOLV-TN and FINSOLV-P (PPG-15 stearyl ether benzoate). Other suitable benzoate esters include Poloxamer 182 Dibenzoate, Poloxamer 105 benzoate and stearyl benzoate. Suitable benzoic acid esters are described for example in U.S. Pat. Nos. 4,275,222; 4,278,655; 4,293,544; 4,322,545; and 4,323,694.

While the amounts of each component of the present solutions will depend on the particular ingredients chosen, generally retinoid solutions in accordance with this disclosure may contain from 0.001 to 10 percent by weight retinoid, 0.003 to 40 percent by weight anhydrous alcohol and 50 to 99 percent by weight cosolvent.

The method of preparing the solution is not critical. Typically, the cosolvents are combined and the retinoid is added with stirring at room temperature until completely solubilized.

The retinoid solution can be used to formulate topical compositions, such as emulsions or suspensions. In particularly useful embodiments, the topical formulations contain a second active ingredient. The second active ingredient can be useful in treating acne, such as antibiotics (e.g., clindamycin, tetracyclone or erythromycin). In particularly preferred embodiments, retinoid solutions in accordance with this disclosure are included in the non-aqueous phase of an emulsion or suspension, the aqueous phase of which contains a water-soluble active that is incompatible with the retinoid. In certain embodiments, thermal stability of an emulsion or suspension formulation containing both a retinoid and clindamycin in combination is achieved using the present retinoid solutions.

The formulation of oil-in-water emulsions or powder suspensions using the present retinoid solutions is within the purities of one skilled in the art given the present disclosure. Typically, an emulsion or suspension is prepared, and a retinoid solution in accordance with this disclosure is added with adequate stirring to provide homogenous incorporation of the solution. Exemplary formulations are provided in the working examples, infra.

In order that those skilled in the art may be better able to practice the compositions and methods described herein in connection with the retinoid solution embodiments, the following examples are given as an illustration of the preparation of the present retinoid solutions and compositions containing them. It should be noted that the invention is not limited to the specific details embodied in the examples.

It has been experimentally determined that tretinoin is not soluble in ethanol in the ratios set forth in Examples A-D:

|  | Example | | | |
| --- | --- | --- | --- | --- |
|  | A | B | C | D |
| Tretinoin | 0.025 | 0.05 | 0.01 | 0.1 |
| Ethanol | 0.750 | 0.80 | 0.30 | 3.0 |

However, it has now been surprisingly found that when a cosolvent is added to compositions containing the same ratios of tretinoin to ethanol, the tretinoin will completely dissolve into a clear solution:

|  | Example | | | |
| --- | --- | --- | --- | --- |
|  | 1 | 2 | 3 | 4 |
| Tretinoin | 0.05 | 0.025 | 0.01 | 0.1 |
| Ethanol | 0.80 | 0.750 | 0.01 | 3.0 |
| IPM | 3.50 | 1.72 | 0.70 | 7.00 |

Examples 1-4 are clear yellow solutions of tretinoin. Isopropyl myristate ("IPM") can be replaced with alkyl benzoate, isopropyl palmitate ("IPP") or diisopropyl adipate to achieve the same results.

|  | Example | | | | | |
| --- | --- | --- | --- | --- | --- | --- |
|  | E | F | G | H | I | J |
| Tretinoin | 0.1 | 0.05 | 0.025 | 0.01 | 0.05 | 0.025 |
| Alkyl benzoate | 9.90 | — | — | 9.90 | — | — |
| IPM | — | 4.95 | — | — | — | — |
| IPM | — | — | 2.475 | — | — | — |
| Diisopropyl Adipate | — | — | — | — | 4.95 | 2.475 |

In Examples E-J where alcohol is not present, the retinoids are not soluble in the esters alone. This further confirms the present finding that retinoids can be solubilized in a small amount of alcohol by using specific cosolvents.

Further exemplary formulations made using retinoid solutions in accordance with this disclosure are presented in Examples 5-9:

|  | Examples | | | | |
| --- | --- | --- | --- | --- | --- |
| Ingredient | 5 | 6 | 7 | 8 | 9 |
| Dionized water | QS | QS | QS | QS | QS |
| Disodium EDTA | 0.40 | 0.4 | 0.4 | 0.4 | 0.4 |
| Carbopol 980 | 0.20 | 0.2 | 0.2 | 0.2 | 0.2 |
| Steareth S-2 | 1.22 | 1.22 | 1.22 | 1.22 | 1.22 |
| Stearate (and) PEG-100 stearate | 0.896 | .896 | .896 | .896 | .896 |
| Cetyl stearyl alcohol | 1.22 | 1.22 | 1.22 | 1.22 | 1.22 |
| Emulsifier 10 | 0.80 | .80 | .80 | .80 | .80 |
| Glycerin | 13.79 | 13.79 | 13.79 | 13.79 | 13.79 |
| Butyl hydroxyl toluene | 0.05 | .05 | .05 | .05 | .05 |
| Sorbic acid | 0.10 | .10 | .10 | .10 | .10 |
| Clindamycin phosphate (100% active) | 1.00 | 1.00 | 1.00 | 1.00 | 1.00 |
| Tretinoic acid | 0.05 | 0.05 | 0.025 | 0.01 | 0.1 |
| Ethyl alcohol, anhydrous | 0.80 | 0.80 | 0.750 | 0.30 | 3.00 |
| IPM | 6.40 | 3.50 | 1.72 | 0.70 | 7.00 |

In examples 5-9 above, IPM can be replaced with alkyl benzoate ($C_{12}$-$C_{15}$ alkyl benzoate) or IPP.

Examples 10 and 11

Emulsion Formulation

Active combination: clindamycin 1.00% w/w; tretinoin 0.05% w/w

| Ingredient | % Ex. 10 | % Ex. 11 |
| --- | --- | --- |
| Dionized water | 71.5626 | 75.6824 |
| Disodium EDTA | 0.4 | 0.5 |
| NaOH (10%) | — | 0.35 |
| Carbopol 980 | 0.20 | 0.65 |
| Steareth S-2 | 1.216 | 1.9 |
| Stearate (and) PEG-100 stearate | 0.896 | 2.5 |
| Cetyl stearyl alcohol | 1.216 | 3.0 |
| Emulsifier 10 | 0.800 | 2.3 |
| Tween 20 | 0.80 | — |
| Fluilan | — | 0.36 |
| Glycerin | 13.79 | 1.9 |
| Butyl hydroxyl toluene | 0.040 | 0.05 |
| Stearaths-21 | — | 1.40 |
| Sorbic acid | 0.08 | 0.10 |
| Clindamycin phosphate (100% active) | 1.00 | 1.255 |
| Tretinoic acid | 0.0504 | 0.526 |
| Ethyl alcohol, anhydrous | 0.80 | 1.0 |
| Alkyl benzoate | 7.149 | — |
| IPM | — | 7.0 |

The emulsions of Example 10 and 11 is prepared as follows: Carbopol 980 is dispersed in water at 70-80° C. Then, dissolve EDTA and mix well. The oil phase is prepared by combining steareth S-2, steareth S-21, tween 20 stearate and PEG-100 stearate, cetyl stearyl alcohol, emulsifier 10, Fluilan butyl hydroxy toluene and sorbic acid in the amounts indicated. The oil phase is heated to 75° C. Add the oil phase to the aqueous phase at 70-80° C. with high shear mixing until a white emulsion is produced. Then cool the batch to room temperature. Dissolve the clindamycin in water and glycerin and add to the emulsion. Prepare a clear solution of tretinoin in alcohol and cosolvent. Add the tretinoin solution to the emulsion phase and continue mixing at high shear until uniform creamy emulsion is produced.

The elevated temperature stability of the actives in the oil in water emulsion of Example 10 was determined using techniques within the purview of those skilled in the art. The results were as follows:

|  | 25° C. | 30° C. |
|---|---|---|
| Clindamycin | | |
| Initial | 0.975% | — |
| 1 month | — | 0.958% |
| 2 months | 0.975% | 0.958% |
| 3 months | 0.975% | 0.958% |
| Tretinoin | | |
| Initial | 0.0497% | — |
| 1 month | — | 0.0490 |
| 2 months | 0.0497 | 0.0490 |
| 3 months | 0.0497 | 0.0490 |

Examples 12 and 13

Liquid to Powder Suspension Systems

Liquid to powder suspension systems are prepared having the following compositions:

| | Example | |
|---|---|---|
| Ingredient | 12 % | 13 % |
| Clindamycin phosphate | 1.00 | 1.00 |
| Water | 15.8 | 15.15 |
| Glycerin | 13.80 | 13.80 |
| Propylene glycol | 14.50 | 14.50 |
| Volatile silicone | 35.0 | 35.00 |
| Modified starch | 15.0 | 15.00 |
| Tretinoin | 0.05 | 0.05 |
| Alcohol | 0.80 | 1.50 |
| Alkyl benzoate | 3.50 | 3.50 |
| BHT | 0.05 | — |
| Tween 20 | 0.50 | 0.50 |

Tretinoin is in a solution using a very small amount of alcohol and cosolvent, alkyl benzoate, IPM, IPP. Clindamycin will be in a clear solution in aqueous media with glycerin and propylene glycol. Both the clindamycin aqueous solution and the ester solution of tretinoin are suspended in the volatile silicone and starch. Both actives stay in one composition without interacting. Upon shaking, the composition delivers a therapeutic amount of the two actives for treating acne. Starch and volatile silicone provide excellent aesthetic vehicles, which upon application to the skin provide aesthetically acceptable liquid powder without any stickiness or tackiness. Furthermore, volatile silicone will evaporate from the skin surface, making the active easily available for acne treatment.

The liquid to powder suspension containing clindamycin and tretinoin is prepared as follows: Prepare a clear solution of tretinoin in alcohol and cosolvent. Prepare a clear solution of clindamycin in water and glycerin. Mix the volatile silicone and starch with a high shear mixer. Add polysorbate 20 and propylene glycol to the oil phase. Add clindamycin solution to the oil phase and continue mixing at high speed (shear). Add tretinoic solution to oil phase and continue mixing with a high shear mixer, until a smooth liquid to powder suspension is produced The elevated temperature stability of the actives in the liquid to powder suspension system of Example 13 was determined using techniques known to those skilled in the art. The results were as follows:

|  | 25° C. | 30° C. |
|---|---|---|
| Clindamycin | | |
| Initial | 1.00% | — |
| 1 month | 0.999% | 0.991% |
| 2 months | 0.990% | 0.977% |
| 3 months | 1.02% | 1.01% |
| Tretinoin | | |
| Initial | 0.0517% | — |
| 1 month | 0.0508 | 0.051 |
| 2 months | 0.0499 | 0.0498 |
| 3 months | 0.0497 | 0.0488 |

Figure 2:
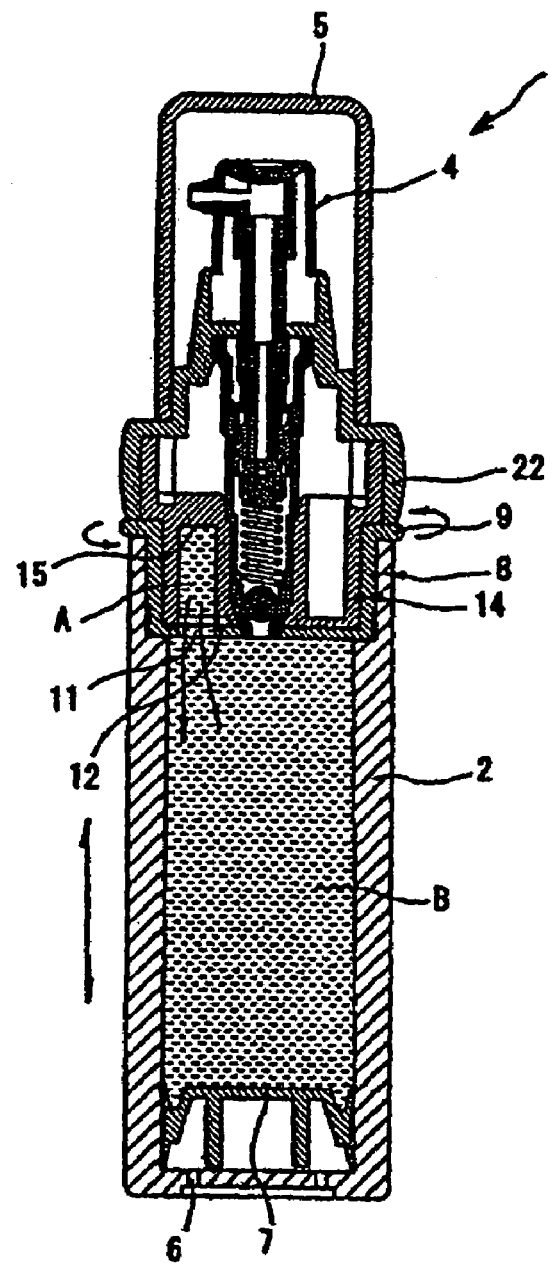
FIG. 2 shows the dispenser of FIG. 1 with the main container twisted to release the composition from the small chamber into the main chamber.
Figure 3:
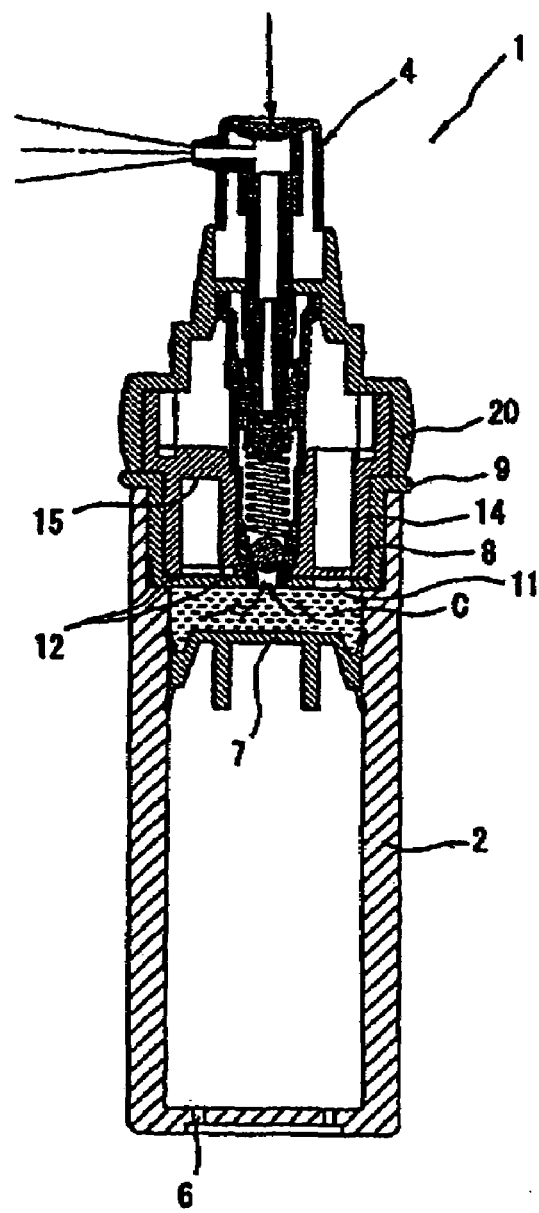
FIG. 3 shows pumping the dispenser of FIG. 1 to dispense a blended composition.

In another embodiment of this disclosure, by utilizing a chamber in a chamber single pump delivery system of the type disclosed in WO 03/082703A1, the disclosure of which is incorporated herein in its entirety, the elevated temperature drug incompatibility is entirely overcome. One of the chambers may include a retinoid solution made in accordance with this disclosure using low levels of alcohol and one or more cosolvents. As seen in FIG. 1, the small chamber 14, which has a small capacity, contains a composition (A) containing one of the active ingredients, such as antibiotics or retinoid. The composition in the small chamber could be either a solution or a powder blend. This chamber is inserted into a main chamber 2, which contains a composition (B) such as a thin lotion, suspension or emulsion, containing the other active ingredient. The small chamber is locked inside the main chamber. The two active drugs never come in contact with each other until the consumer activates the system before use. As shown in FIG. 2, the consumer twists the main container to release the composition from the small chamber into the main chamber. The consumer then will shake the package to blend both products, which are specially formulated with low viscosity to facilitate quick and uniform blending. The consumer can then use the pump delivery mechanism (as shown in FIG. 3) to dispense the blended compositions to deliver the combination of both actives for treating the skin. The ratio of both actives is calculated for this system to deliver the combination of retinoid and antibiotics at a concentration that has already been established as acceptable by the FDA.

The shelf life or expiration date for such products, from the time of manufacturing to the time of patient's total consumption of the dispensed product, will be well over two years since the combined drugs are never exposed to elevated temperatures. Furthermore, this system does not require any overage. The long shelf life and elimination of overage are big advantages from both the FDA perspective as well as the marketing viewpoint.

To effectively utilize the chamber in a chamber delivery system, one must balance the concentration of the actives in both chambers. This is necessary to achieve the final, active concentration, which is efficacious as well as compliant with the FDA. The present disclosure teaches how to prepare higher concentrations of tretinoin in solution for the small chamber by using lower concentrations of alcohol by means of cosolvents such a alkyl benzoate, isopropyl myristate, and isopropyl palmitate. For example, in accordance with the present methods 1 gram of tretinoin can be completely dissolved in only 3 grams of alcohol (33.3 percent solution) by using alkyl benzoate, isopropyl mystirate, isopropyl palmitate, or other esters as cosolvent.

In order that those skilled in the art may be better able to practice the compositions and methods described herein in connection with the chamber in chamber embodiment, the following examples are given as an illustration of the preparation of the present dispensing compositions and system. It should be noted that the invention is not limited to the specific details embodied in the examples.

Example 14

The inner, smaller chamber of a chamber in a chamber package is filled with tretinoin solution composition and the larger, main chamber is filled with a clindamycin emulsion. The formulation for each composition is as follows:

| Small chamber composition | |
|---|---|
| Ingredient | % |
| Tretinoin 100% | 1.00 |
| Anhydrous alcohol | 30.00 |
| Alkyl benzoate | 69.00 |

A. Composition in the Main (Large) Chamber (Clindamycin Emulsion)

| Ingredient | % |
|---|---|
| carbopol 980 | 0.25 |
| glycerin 96% | 2.00 |
| disodium EDTA | 0.50 |
| Di H2O | 78.92 |
| Brij 721 | 1.12 |
| Brij 72 | 1.52 |
| CS-50 | 1.52 |
| Arlacel 165 | 1.52 |
| Emulsifier | 1.84 |
| Fluilan | 0.38 |
| Tween 20 | 1.75 |
| Alkyl benzoate ester | 7.00 |
| Clindamycin PO$_4$ | 1.28 |
| Sorbic acid | 0.10 |
| Germall 115 | 0.30 |
| Ratio of composition A & B | |
| Composition A | 5.00 |
| Composition B | 95.00 |

Once blended, the composition provides clindamycin at 1.0% and tretinoin at 0.05%

Example 15

The inner, smaller chamber of a chamber in a chamber package is filled with tretinoin solution composition and the larger, main chamber is filled with a clindamycin suspension. The formulation for each composition is as follows:
A. Small Chamber Composition—Tretinoin Solution

| Ingredient | % |
|---|---|
| Tretinoin 100% | 1.00 |
| Anhydrous alcohol | 30.00 |
| Alkyl benzoate | 69.00 |

B. Main Chamber Composition—Clindamycin Suspension

| Ingredient | % |
|---|---|
| Clindamycin PO$_4$ (82.7%) | 1.28 |
| H$_2$O | 16.60 |
| Glycerin 99% | 15.46 |
| Propylene glycol | 16.16 |
| Volatile silicone | 35.00 |
| Dry flo | 15.00 |
| Tween 20 | 0.50 |
| Ratio of composition A & B | |
| Composition A: | 5.00 |
| Composition B: | 95.00 |

Once blended, the composition provides Clindamycin at 1.00% and tretinoin at 0.05%.

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

We claim:

1. A clear solution comprising 0.001 to 10% by weight of tretinoin fully dissolved in a solvent system, the solvent system consisting essentially of 0.003 to 40% of an anhydrous alcohol selected from the group consisting of anhydrous ethanol, anhydrous isopropanol and mixtures thereof, and an ester capable of solubilizing the retinoid in the presence of the anhydrous alcohol, the solution containing no free added water, wherein the amount of anhydrous alcohol is insufficient alone to solubilize the amount of tretinoin.

2. A solution as in claim 1 wherein the ester is selected from the group consisting of alkyl benzoate, isopropyl palmitate, diisopropyl adipate, isopropyl myristate and mixtures thereof.

3. A clear solution comprising:
of 0.001 to 10% by weight tretinoin and a solvent system, the solvent system consisting essentially of
(a) 0.003 to 40% by weight of an anhydrous alcohol selected from the group consisting of anhydrous ethanol, anhydrous isopropanol and mixtures thereof, and
(b) alkyl benzoate,
the solution containing no free added water, wherein the amount of anhydrous alcohol is insufficient alone to solubilize the amount of tretinoin.

4. A clear solution comprising:
from 0.001 to 10 percent by weight retinoid fully dissolved in a solvent system, the solvent system consisting essentially of 0.003 to 40 percent by weight of an anhydrous alcohol selected from the group consisting of anhydrous ethanol, anhydrous isopropanol and mixtures thereof, and the balance of the solvent system being an ester capable of solubilizing the retinoid in the presence of the anhydrous alcohol, the solution containing no free added water, wherein the amount of anhydrous alcohol is insufficient alone to solubilize the amount of retinoid present.

5. A composition comprising
a clear, anhydrous solution having 0.001 to 10 percent by weight retinoid fully dissolved in a single phase solvent system, the solvent system comprising 0.003 to 40% of an anhydrous alcohol and an ester capable of solubilizing the retinoid in the presence of the anhydrous alcohol, wherein the amount of anhydrous alcohol is insufficient alone to solubilize the amount of tretinoin present and the amount of ester exceeds the amount of anhydrous alcohol and wherein the amount of retinoid in the solution exceeds the solubility limit of the retinoid in either the alcohol alone or the ester alone.

* * * * *

UNITED STATES PATENT AND TRADEMARK OFFICE
CERTIFICATE OF CORRECTION

PATENT NO.        : 7,662,855 B2                                                Page 1 of 1
APPLICATION NO.   : 10/984630
DATED             : February 16, 2010
INVENTOR(S)       : Mohan Vishnupad et al.

It is certified that error appears in the above-identified patent and that said Letters Patent is hereby corrected as shown below:

Column 9, line 5, (Claim 5):

"tretinoin" should be --retinoid--.

Signed and Sealed this

Twenty-seventh Day of April, 2010

David J. Kappos
*Director of the United States Patent and Trademark Office*